(12) United States Patent  
Almering et al.

(10) Patent No.: US 8,395,002 B2
(45) Date of Patent: Mar. 12, 2013

(54) USE OF CATALYTIC DISTILLATION FOR BENZENE SEPARATION AND PURIFICATION

(75) Inventors: Martinus J. Almering, Houston, TX (US); Purvis K. Ho, Houston, TX (US); Mitchell E. Loescher, Tulsa, OK (US); Montri Vichailak, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 444 days.

(21) Appl. No.: 12/720,173

(22) Filed: Mar. 9, 2010

(65) Prior Publication Data

US 2010/0228063 A1 Sep. 9, 2010

Related U.S. Application Data

(60) Provisional application No. 61/158,592, filed on Mar. 9, 2009.

(51) Int. Cl.
*C07C 5/09* (2006.01)
(52) U.S. Cl. ......... 585/264; 585/259; 585/804; 585/807
(58) Field of Classification Search .................. None
See application file for complete search history.

(56) References Cited

U.S. PATENT DOCUMENTS

| | | | |
|---|---|---|---|
| 4,237,329 A | 12/1980 | Kamiyama et al. | |
| 4,302,356 A | 11/1981 | Smith, Jr. | |
| 4,443,559 A | 4/1984 | Smith, Jr. | |
| 4,463,206 A | 7/1984 | Derrien et al. | |
| 4,731,229 A | 3/1988 | Sperandio | |
| 4,870,222 A | 9/1989 | Bakas et al. | |
| 5,073,236 A | 12/1991 | Gelbein et al. | |
| 5,266,546 A | 11/1993 | Hearn | |
| 5,401,365 A | 3/1995 | Chen et al. | |
| 5,431,890 A | 7/1995 | Crossland et al. | |
| 5,730,843 A | 3/1998 | Groten et al. | |
| 5,773,670 A | 6/1998 | Gildert et al. | |
| 5,856,602 A | 1/1999 | Gildert et al. | |
| 6,407,300 B2 * | 6/2002 | Maraschino | 585/259 |
| 6,677,496 B2 | 1/2004 | Netzer | |
| 2008/0086020 A1 * | 4/2008 | Podrebarac et al. | 585/809 |

OTHER PUBLICATIONS

International Search Report and Written Opinion issued Sep. 28, 2010 in corresponding International application No. PCT/US2010/026612 (6 pages).
Correspondence reporting First Office Action issued Aug. 17, 2012 in corresponding Chinese application No. 201010127666.5 (10 pages).

* cited by examiner

*Primary Examiner* — Tam M Nguyen
(74) *Attorney, Agent, or Firm* — Osha • Liang LLP

(57) ABSTRACT

A process for recovering benzene, the process including: feeding hydrogen and a hydrocarbon fraction comprising benzene, components lighter than benzene, components heavier than benzene, and diolefins to a catalytic distillation reactor system comprising at least one reaction zone comprising a hydrogenation catalyst; concurrently in the catalytic distillation reactor system: contacting the diolefins and hydrogen in the presence of the hydrogenation catalyst to selectively hydrogenate at least a portion of the diolefins; and fractionating the hydrocarbon fraction to form a fraction comprising benzene and other $C_6$ hydrocarbons, and a heavies fraction comprising $C_{7+}$ hydrocarbons; recovering the heavies fraction from the first catalytic distillation reactor system as a bottoms fraction; and withdrawing the fraction comprising benzene and other $C_6$ hydrocarbons from the catalytic distillation reactor system as a benzene concentrate fraction.

23 Claims, 1 Drawing Sheet

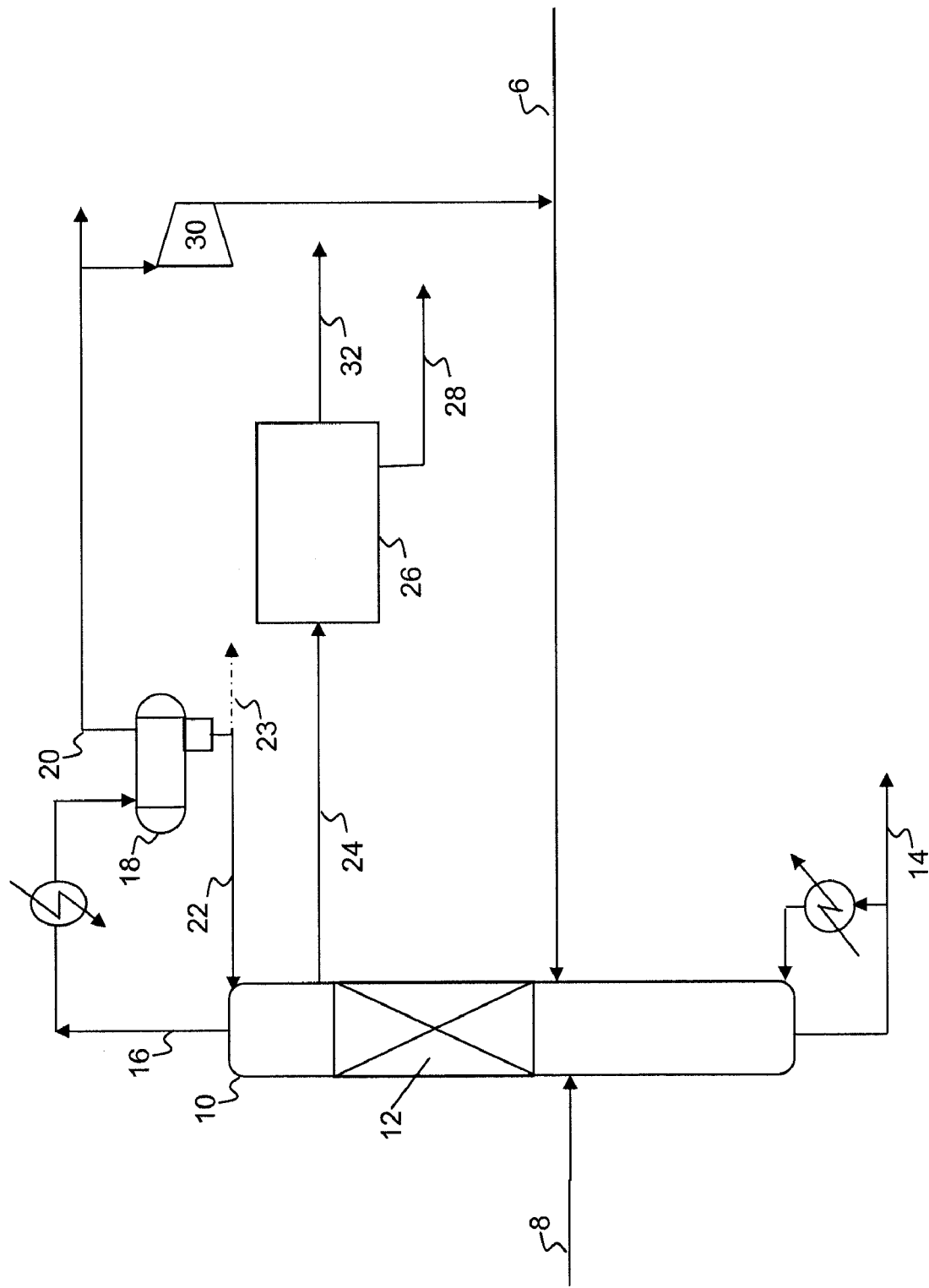

USE OF CATALYTIC DISTILLATION FOR BENZENE SEPARATION AND PURIFICATION

CROSS-REFERENCE TO RELATED APPLICATION

This application, pursuant to 35 U.S.C. §119(e), claims priority to U.S. Provisional Application Ser. No. 61/158,592, filed Mar. 9, 2009. That application is incorporated by reference in its entirety.

BACKGROUND OF DISCLOSURE

1. Field of the Disclosure

Embodiments disclosed herein relate generally to a process for the separation and purification of benzene in a hydrocarbon stream. More specifically, embodiments disclosed herein relate to the selective hydrogenation of diolefins in a hydrocarbon stream, allowing for improved purification and separation of benzene.

2. Background

One common process long used by the refinery industry to upgrade raw naphtha to high octane gasoline is catalytic reforming. In catalytic reforming, the raw naphtha having a boiling range from about 46 to 177° C. (115° F.-350° F.) is passed over an alumina supported noble metal catalyst at elevated temperatures (about 493° C.-565° C. (920° F.-1050° F.)) and moderate pressure (about 2 bar to 39 bar (about 15-550 psig)). The catalyst "reforms" the molecular structures of the hydrocarbons contained in the raw naphtha by removing hydrogen and rearranging the structure of the molecules so as to improve the octane number of the naphtha.

Because of the multiplicity of the compounds in the raw naphtha, the actual reactions which occur in catalytic reforming are numerous. Many of the resulting products are aryl or aromatic compounds, all of which exhibit high octane numbers. The aryl compounds produced depend upon the starting materials which in a refinery are controlled by the boiling range of the naphtha used and the crude oil source. The "reformed" product from a catalytic reforming process is commonly called reformate and is often separated into two fractions by conventional distillations—a light reformate having a boiling range of about 46° C.-121° C. (about 115° F.-250° F.) and a heavy reformate having a boiling range of about 121° C.-177° C. (about 250° F.-350° F.). The aryl compounds in each fraction are thus dependent upon their boiling points. The lower boiling or lighter aryl compounds, e.g., benzene, toluene and xylenes, are contained in the light reformate and higher boiling aryl compounds are contained in the heavy reformate. In other circumstances, the light reformate may contain only the benzene, or only benzene and toluene, depending upon any downstream processing of the stream.

The demand for cleaner and safer transportation fuels is becoming greater every year. Two major sources of gasoline feedstock, including reforming and catalytic cracking, present both a problem meeting strict environmental regulations and impose certain health risks. For example, light reformate typically contains unacceptably high levels of benzene, a known carcinogen and an environmental contaminant. As such, refiners in the U.S and in other countries are required to remove benzene from reformate streams and other gasoline fractions. Refiners may also desire to remove benzene in order to produce the benzene as a product, due to the fact that benzene is valuable for use in chemical processing. For example, benzene is used as an industrial solvent and is also a precursor in the production of pharmaceuticals, plastics, synthetic rubber, and dyes.

U.S. Pat. No. 5,773,670 discloses a process for the hydrogenation of aromatics in a petroleum stream. However, like solvent extraction, the process is not selective to one aromatic compound. U.S. Pat. No. 5,856,602 discloses the hydrogenation of aromatics in a hydrocarbon stream utilizing a distillation column reactor wherein the placement of the catalyst bed and operation of the distillation column controls which aromatic is retained in the catalyst bed for hydrogenation.

The separation and purification of benzene is complicated by the presence of contaminants, such as diolefins. Olefins having more than one double bond (diolefins) have fewer uses than compounds such as ethylene or butane. The removal of diolefins is of value prior to the recovery of benzene since these compounds have been found to be detrimental in most processing, storage, and use of the benzene streams. Various options for the removal of diolefins from such streams may include extraction, hydrogenation, and alkylation. Diolefin hydrogenation may be conducted by contacting diolefins with hydrogen in the presence of a hydrogenation catalyst to convert the diolefins to olefins and paraffins. However, non-selective hydrogenation results in a reduced octane rating and thus diminishes the overall value of the fuel. Thus, selective hydrogenation of diolefins in a benzene-containing reformate is valuable in retaining a high octane rating while reducing diolefin concentrations.

After catalytic reforming of the raw naphtha, benzene may be separated from the lighter aryl compounds by extraction with any number of solvents and separated from other aromatics in the light reformate by distillation, typically using an aromatics extraction unit (AXU). Aromatics extraction is a very old process and typically separates a catalytic reformate or a coke oven light oil, via liquid-liquid extraction or extractive distillation or both, into aromatics and non-aromatics.

It is also conventional, in many catalytic reforming systems, to use a guard bed to provide clay treating of the hydrocarbon feed or the light reformate. A guard bed provides hot or cold clay treating using a fixed-bed, vapor-phase process to polymerize selectively unsaturated gum-forming constituents (i.e., diolefins). A guard bed may be used before or within an AXU and removes trace amounts, typically 10 to 5000 wt ppm, of diolefins present. These diolefins, if not removed, may cause the extracted benzene to fail acid wash color tests, e.g., ASTM D-848. Additionally, diolefins fed to an extraction unit may cause the loss of extraction solvent into the extract product (i.e., benzene), as is well known by those skilled in the aromatics extraction art. For nitrogen-containing extraction solvents, this may make the product benzene off-spec on nitrogen and may place additional load on the clay treaters to remove the lost solvent. However, clay treatment is not without its problems, including the raw material and disposal costs associated with the clay.

Accordingly, there is still a significant need in the art for economical methods to recover benzene from a reformate stream.

SUMMARY OF THE DISCLOSURE

In one aspect, embodiments disclosed herein relate to a process for recovering benzene, the process including: feeding hydrogen and a hydrocarbon fraction comprising benzene, components lighter than benzene, components heavier than benzene, and diolefins to a catalytic distillation reactor system comprising at least one reaction zone comprising a hydrogenation catalyst; concurrently in the catalytic distillation reactor system: contacting the diolefins and hydrogen in the presence of the hydrogenation catalyst to selectively hydrogenate at least a portion of the diolefins; and fractionating the hydrocarbon fraction to form a fraction comprising benzene and other $C_6$ hydrocarbons, and a heavies fraction comprising $C_{7+}$ hydrocarbons; recovering the heavies fraction from the first catalytic distillation reactor system as a bottoms fraction; and withdrawing the fraction comprising benzene and other $C_6$ hydrocarbons from the catalytic distillation reactor system as a benzene concentrate fraction.

In another aspect, embodiments disclosed herein relate to a process for retrofitting a process for reducing the concentration of benzene in a hydrocarbon stream wherein a stream comprising a hydrocarbon fraction comprising benzene, components lighter than benzene, components heavier than benzene, and diolefins is fed to a distillation column to fractionate the hydrocarbon fraction into a benzene concentrate fraction comprising benzene and other $C_6$ hydrocarbons, and a heavies fraction comprising $C_{7+}$ hydrocarbons, wherein the heavies fraction is recovered from the distillation column as a bottoms fraction and the benzene concentrate fraction is withdrawn from the distillation column and fed to an aromatics extraction unit, the process comprising: disposing catalysts formed as a distillation structure within the distillation column; feeding hydrogen to the distillation column; and contacting the diolefins and hydrogen in the presence of a hydrogenation catalyst to selectively hydrogenate at least a portion of the diolefins, wherein contacting the diolefins and hydrogen in the presence of the hydrogenation catalyst is performed concurrently with fractionating the hydrocarbon fraction in the distillation column.

Other aspects and advantages will be apparent from the following description and the appended claims.

BRIEF DESCRIPTION OF DRAWINGS

FIG. 1 is a simplified flow diagram of a process for the separation and purification of benzene from hydrocarbon streams according to embodiments disclosed herein.

DETAILED DESCRIPTION

In one aspect, embodiments herein relate to processes for the separation and purification of benzene in a hydrocarbon stream. More specifically, embodiments disclosed herein relate to processes for the selective hydrogenation of diolefins in a reformate or a cracked hydrocarbon stream, allowing for improved separation and purification of benzene. Processes disclosed herein advantageously separate and treat select portions of the hydrocarbon feed, namely a fraction including benzene. Such benzene-containing fractions may include a $C_6$ cut, a $C_5$-$C_6$ cut, and others. The benzene-containing fraction may then be treated to separate or purify the benzene contained therein. The desired separation and treatment, in some embodiments, may be achieved using a catalytic distillation reactor system.

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

It may be desirable to reduce or remove diolefins in any number of refinery streams. By "complex refinery streams," it is intended to mean the normally liquid product streams found in a refinery from cokers, FCC units, reformers, hydrocrackers, hydrotreaters, delayed cokers, distillation columns, etc. which streams comprise a range of chemical constituents, mainly hydrocarbonaceous, and having a broad boiling point range. The hydrocarbon feed to the processes disclosed herein may be a diolefin- and benzene-containing fraction which boils in the gasoline boiling range, including reformate, FCC gasoline, coker pentane/hexane, coker naphtha, FCC naphtha, straight run gasoline, pyrolysis gasoline, and mixtures containing two or more of these streams. In some embodiments, reformate streams may be undistilled, such as a reformate stream fed directly from a reformer to processes described herein. Such gasoline fractions typically have a normal boiling point within the range of 0° C. and 260° C., as determined by an ASTM D86 distillation. Feeds of this type include light naphthas typically having a boiling range of about $C_6$ to 165° C. (330° F.); full range naphthas, typically having a boiling range of about $C_5$ to 215° C. (420° F.), heavier naphtha fractions boiling in the range of about 125° C. to 210° C. (260° F. to 412° F.), or heavy gasoline fractions boiling in the range of about 165° C. to 260° C. (330° F. to 500° F.). In general, a gasoline fuel will distill over the range of from about room temperature to 260° C. (500° F.). In some embodiments, these streams may be treated to remove sulfur, nitrogen, and other undesired components. For convenience, each of these various complex refinery streams will be referred to herein as reformate.

Reformate fractions for use in embodiments of the hydrogenation processes described herein may include $C_3$ to $C_9$ and higher hydrocarbons. For example, refinery streams may be separated by fractional distillation, recovering a certain fraction for further processing. A light naphtha cut is one such refinery stream, and because such a cut often contains compounds that are very close in boiling points, the separations are not precise. The light naphtha refinery cut is valuable as a source of isoolefins ($iC_5$=and $iC_6$=compounds, for example) for forming an ether by reaction with ethanol. Thus, a $C_5$ stream, for instance, may include $C_4$s and up to $C_8$s and higher. These components may be saturated (alkanes), unsaturated (mono-olefins, including isoolefins), and poly-unsaturated (diolefins, for example). Additionally, the components may be any or all of the various isomers of the individual compounds. Such a mixture may easily contain 150 to 200 components. Other hydrocarbon streams of $C_4$ to $C_9$ carbon atoms may be used in embodiments disclosed herein.

In some embodiments, gasoline fractions may include a $C_4$ cut, which may include $C_3$ to $C_5$ or higher hydrocarbons (i.e., $C_{6+}$). In other embodiments, gasoline fractions may include a $C_5$ cut, which may include $C_4$ to $C_8$ or higher hydrocarbons, including olefins. In other embodiments, gasoline fractions may include a $C_6$ cut, which may include $C_4$ to $C_9$ or higher hydrocarbons, including olefins. In other various embodiments, gasoline fractions may include mixtures of one or more of $C_4$, $C_5$, $C_6$, and $C_{7+}$ hydrocarbons, where the mixture includes olefinic and diolefinic compounds. The above described streams may include $C_4$ to $C_7$ streams, FCC gasoline, pyrolysis gasoline, coker gasoline, and other refinery streams having similar properties.

Saturated compounds included in the above described gasoline fractions may include various isomers of butane, various isomers of pentane, and various isomers of hexane, among others, for example. Olefinic compounds included in the above described gasoline fractions may include isobutylene and other butene isomers, various isomers of pentene, various isomers of hexene, and various isomers of heptene, among others, for example. Aromatic compounds that may be included in the above described gasoline fractions may include benzene, toluene, xylenes, ethylbenzene, cumenes, and other various derivatives of benzene, such as polyalkylated benzene (ethyl methyl benzene, diethyl benzene, etc.).

In accordance with some embodiments, a light reformate may include a complex aromatics-containing stream containing a minor amount of benzene, produced in a refinery reforming unit, and generally having a boiling point range of 15° C. to 104° C. (60° F. to 220° F.). In such instances the benzene concentration of the light aromatics-containing streams may range from about 1% to 40% by volume in some embodiments; between about 2% and 30% in other embodiments; and between about 5% and 25% in yet other embodiments.

In some embodiments, a full boiling range reformate may be used as the process feed. In such instances the reformate will generally have a boiling point range of 15° C. to 204° C. (60 to 400° F.), and the benzene concentration of the full boiling range aromatics-containing stream may range from about 1% to 20% by volume in some embodiments; between about 2% and 15% in other embodiments; and between about 3% and 10% in yet other embodiments. The concentration of olefins in these streams may vary, and may range from about 5% to 40% olefin by volume; and between about 10% and 30% by volume in other embodiments. The concentration of diolefins in these streams may vary, and may range from about 0.1 to about 30 percent by volume in various embodiments, and from 1 to about 10 weight percent in other embodiments.

While removal of diolefins is a primary goal of the processes disclosed herein, it may also be desirable to limit saturation of olefins and aromatics contained within the hydrocarbon feed. In other embodiments, hydrocarbon streams containing diolefins may also contain other compounds that may negatively affect catalyst performance, such as acetylenes, and other bad actors that may poison catalysts used herein or result in excessive polymer formation on the catalyst surface. Embodiments disclosed herein may provide for one or more of reduced olefin saturation, reduced saturation of toluene and higher molecular weight aromatics, extended catalysts service life and decreased costs associated with treatment of the feed streams to remove catalyst poisons and other bad actors.

Processes disclosed herein advantageously selectively hydrogenate diolefins in a select portion of the hydrocarbon feed, namely a fraction including benzene. Such benzene-containing fractions may include a $C_6$ cut, a $C_5$-$C_6$ cut, and a $C_4$-$C_6$ cut, among others. The benzene cut, following the selective hydrogenation of diolefins, may be sent to an aromatics extraction unit (AXU) for further separation and purification of the benzene. The AXU processes the benzene cut using liquid-liquid extraction or extractive distillation or both, into a benzene stream and a stream containing components lighter than benzene.

Processes disclosed herein may include any number of reactors, including catalytic distillation reactor systems, both up-flow and down-flow. Use of catalytic distillation reactor systems may prevent foulants and heavy catalyst poisons in the feed from contacting the catalyst. In addition, clean hydrogenated reflux may continuously wash the catalyst zone. These factors combine to provide a long catalyst life. The heat of reaction evaporates liquid and the resulting vapor is condensed in the overhead condenser to provide additional reflux. The natural temperature profile in the fractionation column results in a virtually isothermal catalyst bed rather than the temperature increase typical of conventional fixed bed reactors.

Any catalyst useful for the selective hydrogenation of diolefins may be used in the processes disclosed herein. Among the metals known to catalyze the hydrogenation reaction are platinum, rhenium, cobalt, molybdenum, nickel, tungsten and palladium. For example, the hydrogenation catalyst may include substantially any catalyst capable of catalyzing the hydrogenation of diolefins to olefins and paraffins. Such a catalyst may include a Group VIII metal, which may be supported on a porous inorganic oxide support, for example. Group VIII metals of the Periodic Table of Elements, such as platinum and palladium may be used as the principal catalytic component, alone or with promoters and modifiers such as palladium/gold, palladium/silver, and cobalt/zirconium. Such catalysts may be deposited on a support, such as alumina, fire brick, pumice, carbon, resin, silica, an aluminosilicate, such as a zeolite or the like. Generally, commercial forms of catalyst use supported oxides of these metals. The oxide is reduced to the active form either prior to use with a reducing agent or reduced during use by the hydrogen in the feed. Specific examples of hydrogenation catalysts useful in embodiments herein include platinum on alumina and platinum on a zeolite with alumina binder added for strength. Suitable zeolites include X, Y, faujasite, mordenite, and synthetic aluminosilicates, among others.

When used in a catalytic distillation reactor system, to facilitate fractionation and catalytic activity, the above described catalysts may be prepared in the form of a distillation structure. The catalytic distillation structure must be able to function as catalyst and as mass transfer medium. The catalyst must be suitably supported and spaced within the column to act as a catalytic distillation structure.

In some embodiments, the catalyst is contained in a structure as disclosed in U.S. Pat. No. 5,730,843, which is hereby incorporated by reference. In other embodiments, one or more of the above-described catalysts may be contained in a plurality of wire mesh tubes closed at either end and laid across a sheet of wire mesh fabric such as demister wire. The sheet and tubes are then rolled into a bale for loading into the distillation column reactor. This embodiment is described, for example, in U.S. Pat. No. 5,431,890, which is hereby incorporated by reference. Other useful catalytic distillation structures are disclosed in U.S. Pat. Nos. 4,302,356, 4,443,559, 4,731,229, 5,073,236, 5,431,890, 5,266,546, and 5,730,843, which are each incorporated by reference.

Referring now to FIG. 1, a simplified process flow diagram of a process for the separation and purification of benzene from hydrocarbon streams, according to embodiments disclosed herein, is illustrated. Selective hydrogenation of diolefins according to embodiments disclosed herein may be attained by feeding hydrogen 6 and a diolefin- and benzene-containing hydrocarbon fraction 8 to a catalytic distillation reactor system 10 including at least one reaction zone 12 containing a hydrogenation catalyst, where the at least one reaction zone 12 is located in an upper portion of the catalytic distillation reactor system. Benzene-containing hydrocarbon fraction 8 may include components lighter than benzene, benzene, and components heavier than benzene. Hydrogen 6 and benzene-containing hydrocarbon fraction 8 may be fed to the catalytic distillation reactor system 10 at a location below reaction zone 12, such that $C_6$ and lighter components, including benzene and diolefins, may distill upward into the reaction zone. The $C_7$ and heavier components, including toluene, may be distilled downward, avoiding or minimizing contact of $C_{7+}$ aromatic compounds with the hydrogenation catalyst in reaction zone 12. At least a portion of the diolefins and hydrogen may then react to form olefins and paraffins.

The operation of the catalytic distillation column should be such that reaction conditions suitable for the selective hydrogenation of diolefins are achieved in the reaction zone(s). The distillation column reactor is operated at a pressure such that a reaction mixture is boiling in the bed of catalyst. Catalytic distillation reactor system 10 may operate at an overhead pressure in the range between 1 bar and 25 bar (about 0 to 350 psig), such as 18.3 bar or less (250 psig or less) in some embodiments, and 3.4 to 9.3 bar (35 to 120 psig) or 6.5 to 9.3 bar (80 to 120 psig) in other embodiments. Temperatures in distillation column reactor system 10 may be in the range from 38° C. to 260° C. (100 to 500° F.) in some embodiments; from 65° C. to 204° C. (150° F. to 400° F.) in other embodiments; from 93° C. to 191° C. (200° F. to 375° F.) in other embodiments; and from 127° C. to 138° C. (260° F. to 280° F.) in yet other embodiments, each at the requisite hydrogen partial pressures. Under these conditions the $C_6$ fraction may be maintained in the hydrogenation catalyst zone a sufficient time to obtain diolefin conversions of over 80 percent, usually over 90 percent, but may be as low as 50 percent. The feed weight hourly space velocity (WHSV), which is herein understood to mean the unit weight of feed per hour entering the reaction distillation column per unit weight of catalyst in the catalytic distillation structures, may vary over a very wide range within the other condition perimeters, e.g., from about 0.1 to about 35. The overhead pressure of the column will vary depending upon the reaction temperature, and should be maintained so as to attain the desired reduction in diolefin concentration.

Catalytic distillation reactor system 10 may include conventional trays or packing both above and below reaction zone 12, providing for separation of the feed components. The $C_7$ and heavier components may be recovered from distillation column reactor system 10 as a first bottoms fraction 14. The $C_6$ components may be recovered from distillation column reactor system 10 as a $C_6$ fraction in flow line 24.

In some embodiments, a light fraction, such as a $C_3$, a $C_4$, or a $C_4$-$C_5$ cut may be recovered from distillation column reactor system 10 as a first overheads fraction 16, along with any unreacted hydrogen. Overheads fraction 16 may then be cooled and at least partially condensed, where the resulting liquid and vapor phases may be separated in drum 18. Hydrogen and non-condensed lights, such as methane, ethane, and other light hydrogenation by-products, may be recovered via flow line 20. Condensed liquids may be returned to the column as a total reflux via flow line 22. Hydrogen in overheads fraction 20 may be pressurized via compressor 30 and returned to the catalytic distillation reactor system 10 via flow line 6. In this manner, hydrogen may be efficiently used and recycled within the system with minimal compressor duty.

The $C_6$ fraction 24 may be a fraction including $C_4$-$C_6$ hydrocarbons, such as a $C_6$ cut, or a $C_5$-$C_6$ cut, for example. The $C_6$ fraction 24 may then be sent to an AXU 26 to recover benzene. The AXU 26 may process the $C_6$ fraction using liquid-liquid extraction or extractive distillation or both. The benzene product may be recovered from AXU 26 as a benzene fraction 28. Remaining $C_4$-$C_6$ components are recovered from the AXU 26 as a raffinate flow 32.

In other embodiments, a portion of the condensed liquids may be recovered as an overheads fraction via flow line 23. For example, $C_4$ or $C_5$ and lighter hydrocarbons, separated from the hydrogen in drum 18, may be recovered and further processed separate from the $C_6$ fraction, where column 10 is operated under partial reflux. Recovery of a $C_5$ or a $C_4$ and lighter fraction as an overhead fraction may be desired, for example, to minimize hydrogenation of light olefins contained within such fractions.

As mentioned above, conventional processes for the separation and purification of benzene may include the use of a guard bed for the removal of diolefins. For example, a conventional process may include the fractionation of a hydrocarbon fraction comprising benzene, components lighter than benzene, components heavier than benzene, and diolefins in a distillation column. The fractionation may result in the recovery of a fraction comprising benzene and other $C_6$ hydrocarbons and a heavies fraction comprising $C_{7+}$ hydrocarbons, for example. The fraction comprising benzene may then be passed through a guard bed to remove diolefins. A guard bed may be used before or within an AXU to remove diolefins. For example, the $C_6$ fraction may be passed through a guard bed containing zeolites or other appropriate absorbents to remove dienes and other components which may result in the product failing acid wash color tests (e.g., ASTM D-848) or causing the loss of extraction solvent into the extract product. As the guard bed typically treats large fractions, it may be very large itself. The size of the guard bed may increase costs associated with the benzene recovery process, such as for the disposal of the clay.

For such existing processes, embodiments disclosed herein may allow for a significant decrease in the size of the guard bed or eliminate the need for a guard bed entirely. For example, selective hydrogenation catalyst, formed as a distillation structure, may be disposed in an existing fractionation tower. Additionally, a hydrogen feed may be supplied to the tower. In this manner, during fractionation of the hydrocarbon feed, diolefins and hydrogen may be contacted in the presence of the hydrogenation catalyst to hydrogenate at least a portion of the diolefins. Due to the hydrogenation of diolefins, existing guard beds may be taken out of service, reduced in size, or may have longer service times, thus reducing or eliminating adsorbent usage and disposal costs.

Additionally, the existing AXU may include a post-extraction fractionation unit. Because of the selective hydrogenation of diolefins achieved using embodiments disclosed herein, along with the pre-fractionation of heavier aromatics, embodiments disclosed herein may also reduce or eliminate the need for post-extraction fractionation in the AXU.

Selective hydrogenation of diolefins according to embodiments disclosed herein, such as by processes according to FIG. 1, may effectively reduce or eliminate diolefins in the $C_6$ fraction recovered via flow lines 24, and the extracted benzene 28. In some embodiments, the recovered $C_6$ fraction 24 may contain less than 1000 ppm diolefins; less than 500 ppm in other embodiments; less than 250 ppm in other embodiments; less than 100 ppm in other embodiments; and less than 50 ppm in yet other embodiments In other embodiments, diolefins may not be present in the recovered light hydrocarbon fraction at detectable limits.

As described above, embodiments described herein may provide for the separation and purification of benzene from a hydrocarbon stream. Advantageously, embodiments disclosed herein may provide for the efficient reduction of diolefins in a hydrocarbon stream. In some embodiments, the hydrogenation of a select portion of a hydrocarbon stream may allow for efficient catalyst usage, allowing for a reduced amount of catalyst to be used per unit volume of total feed while achieving low diolefin levels. Likewise, separation and hydrogenation of a select portion of a hydrocarbon stream may allow for a reduced guard bed size due to the reduced volume of hydrocarbons being treated, and may even allow for removal of guard beds from a benzene or aromatics extraction unit. Additionally, through separation of $C_7$ and other heavier aromatic compounds, hydrogenation of toluene, xylenes, cumene, and other heavier aromatic compounds may be minimized, thus preserving these high-octane value components for use in the gasoline pool.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for recovering benzene, the process comprising:
    feeding hydrogen and a hydrocarbon fraction comprising benzene, components lighter than benzene, components heavier than benzene, and diolefins to a catalytic distillation reactor system comprising at least one reaction zone comprising a hydrogenation catalyst;
    concurrently in the catalytic distillation reactor system:
        contacting the diolefins and hydrogen in the presence of the hydrogenation catalyst to selectively hydrogenate at least a portion of the diolefins; and
        fractionating the hydrocarbon fraction to form a fraction comprising benzene and other $C_6$ hydrocarbons, and a heavies fraction comprising $C_7+$ hydrocarbons;
    recovering the heavies fraction from the catalytic distillation reactor system as a bottoms fraction;
    withdrawing the fraction comprising benzene and other $C_6$ hydrocarbons from the catalytic distillation reactor system as a benzene concentrate fraction;
    feeding the benzene concentrate fraction to an aromatics extraction unit;
    extracting benzene from the benzene concentrate fraction; and
    recovering a $C_6$ hydrocarbon fraction having a reduced benzene concentration.

2. The process of claim 1, wherein the $C_6$ hydrocarbon fraction having a reduced benzene concentration has a benzene content of less than 100 ppm, by weight.

3. The process of claim 1, wherein the benzene concentrate fraction has a diolefin content of 100 ppm or less.

4. The process of claim 1, wherein the benzene concentrate fraction has a color-causing species content of 100 ppm or less.

5. The process of claim 1, wherein the process is absent at least one of a hot clay treater, a cold clay treater, and a post-fractionation section following the aromatics extraction unit.

6. The process of claim 1, further comprising:
    recovering the benzene concentrate fraction as an overheads fraction from the catalytic distillation reactor system, wherein the benzene concentrate fraction further comprises light hydrocarbons comprising at least one of $C_3$, $C_4$ and $C_5$ hydrocarbons;
    condensing and separating the light hydrocarbons from unreacted hydrogen;
    recovering the unreacted hydrogen; and
    returning the condensed light hydrocarbons to the catalytic distillation reactor system as a total reflux.

7. The process of claim 6, wherein the fraction lighter than the benzene concentrate fraction is essentially free of benzene.

8. The process of claim 1, wherein the fractionating the hydrocarbon fraction further comprises forming a fraction lighter than the benzene concentrate fraction and comprising at least one of $C_3$, $C_4$ and $C_5$ hydrocarbons.

9. The process of claim 1, wherein the fractionating the hydrocarbon fraction further comprises recovering unreacted hydrogen and light hydrocarbons comprising at least one of $C_3$, $C_4$ and $C_5$ hydrocarbons as an overheads fraction from the catalytic distillation reactor system.

10. The process of claim 1, wherein the catalytic distillation reactor system is a divided wall distillation column, wherein at least one section of the divided wall distillation column comprises at least one reaction zone comprising a hydrogenation catalyst.

11. The process of claim 1, wherein the hydrocarbon fraction and the hydrogen are fed to the catalytic distillation reactor system at a location below the at least one reaction zone.

12. A process for retrofitting a process for reducing the concentration of benzene in a hydrocarbon stream, wherein a hydrocarbon fraction comprising benzene, components lighter than benzene, components heavier than benzene, and diolefins is fed to a distillation column to fractionate the hydrocarbon fraction into a benzene concentrate fraction comprising benzene and other $C_6$ hydrocarbons, and a heavies fraction comprising $C_{7+}$ hydrocarbons, wherein the heavies fraction is recovered from the distillation column as a bottoms fraction and the benzene concentrate fraction is withdrawn from the distillation column and fed to an aromatics extraction unit, the process comprising:
    disposing catalysts formed as a distillation structure within the distillation column;
    feeding hydrogen to the distillation column; and
    contacting the diolefins and hydrogen in the presence of a hydrogenation catalyst to selectively hydrogenate at least a portion of the diolefins, wherein contacting the diolefins and hydrogen in the presence of the hydrogenation catalyst is performed concurrently with fractionating the hydrocarbon fraction in the distillation column.

13. The process of claim 12, wherein the process for reducing the concentration of benzene in a hydrocarbon stream includes contacting the hydrocarbon fraction with a guard bed for adsorbing color-containing species, the retrofitting process further comprising:
    taking the guard bed for adsorbing color-containing species out of service.

14. The process of claim 12, further comprising:
    extracting benzene from the benzene concentrate fraction in the aromatics extraction unit; and
    recovering a $C_6$ hydrocarbon fraction having a reduced benzene concentration.

15. The process of claim 12, further comprising:
    recovering the benzene concentrate fraction as an overheads fraction from the distillation column, wherein the benzene concentrate fraction further comprises light hydrocarbons comprising at least one of $C_3$, $C_4$ and $C_5$ hydrocarbons;
    condensing and separating the light hydrocarbons from unreacted hydrogen;
    recovering the unreacted hydrogen; and
    returning the condensed light hydrocarbons to the catalytic distillation reactor system as a total reflux.

16. The process of claim 12, wherein the fractionating a hydrocarbon fraction further comprises forming a fraction lighter than the benzene concentrate fraction and comprising at least one of $C_3$, $C_4$ and $C_5$ hydrocarbons.

17. The process of claim 12, wherein the fractionating a hydrocarbon fraction further comprises recovering unreacted hydrogen and light hydrocarbons comprising at least one of $C_3$, $C_4$ and $C_5$ hydrocarbons as an overheads fraction from the catalytic distillation reactor system.

18. The process of claim 14, wherein the $C_6$ hydrocarbon fraction having a reduced benzene concentration has a benzene content of less than 100 ppm, by weight.

19. The process of claim 14, wherein the benzene concentrate fraction has a diolefin content of 100 ppm or less.

20. The process of claim 14, wherein the benzene concentrate fraction has a color-causing species content of 100 ppm or less.

21. The process of claim 12, wherein the hydrocarbon fraction and the hydrogen are fed to the distillation column at a location below the distillation structure.

22. The process of claim 16, wherein the fraction lighter than the benzene concentrate fraction is essentially free of benzene.

23. The process of claim 13, wherein the aromatics extraction unit comprises a post-extraction fractionation section, the retrofitting process further comprising taking at least a portion of the post-extraction fractionation section out of service.

* * * * *